US006312645B1

(12) United States Patent
Lin et al.

(10) Patent No.: US 6,312,645 B1
(45) Date of Patent: Nov. 6, 2001

(54) CONTAINER WITH COLLAPSIBLE POUCH FOR CLEANING OR STERILIZATION

(75) Inventors: Szu-Min Lin, Laguna Hills; Paul Jacobs, Trabuco Canyon; Alfredo M. Choperena, San Juan Capistrano, all of CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

(21) Appl. No.: 09/222,859

(22) Filed: Dec. 30, 1998

(51) Int. Cl.[7] .................................................. A01N 1/00
(52) U.S. Cl. ............................ 422/33; 422/28; 422/29; 422/33; 422/294; 422/295; 604/411; 604/415
(58) Field of Search ..................... 422/28, 29, 33, 422/294, 295, 411; 604/415

(56) References Cited

U.S. PATENT DOCUMENTS

| | | | |
|---|---|---|---|
| 3,814,901 | 6/1974 | Morhack | 219/401 |
| 4,203,943 | 5/1980 | Gillis et al. | 422/27 |
| 4,321,232 | 3/1982 | Bithell | 422/23 |
| 4,337,223 | 6/1982 | Kaye | 422/112 |
| 4,380,530 | 4/1983 | Kaye | 422/300 |
| 4,410,492 | 10/1983 | Kaye | 422/27 |
| 4,526,622 | 7/1985 | Takamura et al. | 134/21 |
| 4,526,623 | 7/1985 | Ishii et al. | 134/21 |
| 4,576,650 | 3/1986 | Yabe et al. | 134/22.12 |
| 4,576,792 | 3/1986 | Martensson | 422/27 |
| 4,579,597 | 4/1986 | Sasa et al. | 134/21 |
| 4,579,598 | 4/1986 | Sasa et al. | 134/22.12 |
| 4,731,222 | 3/1988 | Kralovic et al. | 422/37 |
| 4,744,951 | 5/1988 | Cummings et al. | 422/28 |
| 4,756,882 | 7/1988 | Jacobs et al. | 422/23 |
| 4,892,706 | 1/1990 | Kralovic et al. | 422/28 |
| 4,937,046 | 6/1990 | Andersen et al. | 422/34 |
| 4,943,414 | 7/1990 | Jacos et al. | 422/28 |
| 4,956,145 | 9/1990 | Cummings et al. | 422/28 |
| 5,017,241 | 5/1991 | Ryan | 134/22.12 |
| 5,037,623 | 8/1991 | Schneider et al. | 422/292 |
| 5,077,008 | 12/1991 | Kralovic et al. | 422/37 |
| 5,091,343 | 2/1992 | Schneider et al. | 422/297 |
| 5,114,596 | 5/1992 | Laterra | 210/798 |
| 5,116,575 | 5/1992 | Badertscher et al. | 422/28 |
| 5,186,893 | 2/1993 | Moulton et al. | 422/23 |
| 5,209,909 | 5/1993 | Siegal et al. | 422/292 |
| 5,217,698 | 6/1993 | Siegel et al. | 422/295 |
| 5,225,160 | 7/1993 | Sanford et al. | 422/28 |
| 5,260,021 | 11/1993 | Zeleznick | 422/28 |
| 5,266,275 | 11/1993 | Faddis | 422/116 |
| 5,279,799 | 1/1994 | Moser | 422/292 |
| 5,310,524 | 5/1994 | Campbell et al. | 422/33 |
| 5,348,711 | 9/1994 | Johnson et al. | 422/28 |
| 5,350,563 | 9/1994 | Kralovic et al. | 422/28 |
| 5,374,394 | 12/1994 | Kralovic | 422/28 |
| 5,391,360 | 2/1995 | Kochte et al. | 422/292 |
| 5,407,648 | 4/1995 | Allen et al. | 422/297 |
| 5,407,685 | 4/1995 | Malchesky et al. | 424/449 |
| 5,441,707 | 8/1995 | Lewis et al. | 422/300 |
| 5,443,801 | 8/1995 | Langford | 422/294 |

(List continued on next page.)

*Primary Examiner*—Robert J. Warden, Sr.
*Assistant Examiner*—Imad Soubra
(74) *Attorney, Agent, or Firm*—Knobbe, Martens, Olson & Bear, LLP

(57) ABSTRACT

The present invention provides a method and apparatus for sanitizing a device, such as an endoscope, having a lumen. The method comprises a) providing a container possessing two or more openings, and a flexible, gas-impermeable pouch that surrounds the container; b) placing the device into the container; c) applying a reduced pressure to the container and pouch, thereby causing the pouch to collapse around the container and form at least one interface separating the container into two or more compartments, which interface is formed under reduced pressure by the adherence of the pouch onto itself and around part of a surface of the device, through openings in the container, such that one end of the device is located in one of the compartments and the other end is in another compartment; and d) generating a flow of a sanitizing solution through the lumen to sanitize the inner surface of the device.

27 Claims, 3 Drawing Sheets

U.S. PATENT DOCUMENTS

| | | | |
|---|---|---|---|
| 5,445,792 | 8/1995 | Rickloff et al. | 422/28 |
| 5,492,671 | 2/1996 | Krafft | 422/26 |
| 5,494,530 | 2/1996 | Graf | 134/18 |
| 5,505,218 | 4/1996 | Steinhauser et al. | 134/95.1 |
| 5,508,009 | 4/1996 | Rickloff et al. | 422/292 |
| 5,527,508 | 6/1996 | Childers et al. | 422/33 |
| 5,534,221 | 7/1996 | Hillebrenner et al. | 422/33 |
| 5,540,901 | 7/1996 | Riley | 422/300 |
| 5,552,115 | 9/1996 | Malchesky | 422/28 |
| 5,556,607 | 9/1996 | Childers et al. | 422/300 |
| 5,580,530 * | 12/1996 | Kowatsch et al. | 422/102 |
| 5,609,821 | 3/1997 | Grimberg et al. | 422/28 |
| 5,667,753 * | 9/1997 | Jacobs et al. | 422/29 |
| 5,674,450 * | 10/1997 | Lin et al. | 422/29 |
| 5,711,921 | 1/1998 | Langford | 422/292 |
| 5,784,466 | 7/1998 | Klayman | 381/24 |

* cited by examiner

CONTAINER WITH COLLAPSIBLE POUCH FOR CLEANING OR STERILIZATION

BACKGROUND OF THE INVENTION

This invention relates to systems and processes for cleaning, chemical sterilizing or disinfecting medical devices.

Medical instruments have traditionally been sterilized or disinfected using either heat, such as is provided by steam, or a chemical in liquid, gas, or vapor state. Prior to sterilization or disinfection, the instruments to be treated are usually first cleaned. After sterilization or disinfection with a liquid chemical germicide, sterile water is used to rinse the instruments, and then the instruments are dried. Numerous publications regarding the cleaning of medical devices and the sterilizing of medical devices are available.

U.S. Pat. No. 5,443,801 discloses a transportable cleaning/sterilizing apparatus and method for inside-outside washing and sterilization of medical/dental instruments. The apparatus functions in four sequential cycles: wash, rinse, sterilize, and dry. The sterilization step is conducted using ozonated and sterile water, and the drying step is accomplished by injecting ozonated/deozonated sterile warm dry oxygen, or sterile inert gas into and exhausted from the wash chamber under a positive pressure relative to atmospheric. In this process, the device has to be rinsed with sterile water after it is sterilized to remove sterilant residue before drying step.

U.S. Pat. No. 5,505,218 to Steinhauser et al. discloses a device for cleaning, disinfecting and maintaining medical or dental instruments. The device has a pot-shaped container with a multiplicity of mountings in the interior of the container each for one of tool holder, a water supply system, a compressed air supply system, and an ultrasonic transducer. The disinfection is conducted with heated water, and the drying is conducted with hot compressed air. This system is not designed for sterilization. U.S. Pat. No. 5,279,799 to Moser et al. discloses apparatus for cleaning and testing endoscopes by injecting pressurized air into the sheath and pressurized air and washing liquid into the ducts. A washing chamber is provided which contains retractable cages to hold the endoscopes during cleaning and testing. This process includes washing, disinfecting, final rinsing with sterile water, and air drying the ducts of a tubular article. A number of filters are involved in this system, and this system is not designed for sterilization.

U.S. Pat. No. 4,744,951 to Cummings et al. discloses a two-chambered system that provides hydrogen peroxide in vapor form for use in sterilization processes. The sterilant is initially vaporized in one chamber and then applied to the object to be sanitized in another single sterilizing chamber, thereby producing a concentrated hydrogen peroxide vapor which is relatively more effective. The sterilization processes are designed for furnishing concentrated hydrogen peroxide vapor to interior surfaces of articles having a tortuous or a narrow path. However, the sterilization processes are ineffective at rapidly sterilizing lumen devices, since they depend on the diffusion of the hydrogen peroxide vapor into the lumen to effect sterilization.

U.S. Pat. No. 4,863,688 to Schmidt et al. discloses a sterilization system consisting of a liquid hydrogen peroxide vaporization chamber and an enclosure for sterilization. The enclosure additionally may hold containers wherein the hydrogen peroxide sterilant vapor does not contact the interior of the containers. This system is designed for controlling the exposure to the hydrogen peroxide vapor. The system is not designed for sterilizing a lumen device.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized.

U.S. Pat. Nos. 4,937,046, 5,118,471 and 5,227,132 to Anderson et al. each disclose a sterilization system that uses ethylene oxide gas for sanitation purposes. The gas is initially in a small first enclosure and thereafter slowly permeates into a second enclosure where the objects to be sterilized are located. A medium is then introduced into the second enclosure to flush out the sterilizing gas into a third enclosure containing the second enclosure. An exhaust system then exhausts the sterilant gas and air from the third enclosure. These systems also have the disadvantage of relying on the diffusion of the sterilant vapor to effect sterilization and hence are not suitable for rapidly sterilizing lumen devices.

U.S. Pat. No. 5,122,344 to Schmoegner discloses a chemical sterilizer system for sterilizing items by vaporizing a liquid chemical sterilant in a sterilizing chamber. Pre-evacuation of the sterilizer chamber enhances the sterilizing activity. Sterilant is injected into the sterilizer chamber from a second prefilled shot chamber. This system also relies upon diffusion of sterilant vapor to effect sterilization and is also not suitable for rapidly sterilizing lumen devices.

U.S. Pat. No. 5,266,275 to Faddis discloses a sterilization system for disinfecting instruments. The sterilization system contains a primary sterilization chamber and a secondary safety chamber. The secondary safety chamber provides for sensing and venting to a destruction chamber any sterilization agent that is released from the primary sterilization chamber. This system, as in other systems, also relies upon diffusion of sterilant vapor to effect sterilization and is also not suitable for rapidly sterilizing lumen devices.

In U.S. Pat. Nos. 5,492,672 and 5,556,607 to Childers et al, there is disclosed a process and apparatus respectively for sterilizing narrow lumens. This process and apparatus uses a multicomponent sterilant vapor and requires successive alternating periods of flow of sterilant vapor and discontinuance of such flow. A complex apparatus is used to accomplish the method. Additionally, the process and apparatus of '672 and '607 require maintaining the pressure in the sterilization chamber at a predetermined subatmospheric pressure.

In U.S. Pat. No. 5,527,508 to Childers et al., a method of enhancing the penetration of low vapor pressure chemical vapor sterilants into the apertures and openings of complex objects is disclosed. The method repeatedly introduces air or an inert gas into the closed sterilization chamber in an amount effective to raise the pressure to a subatmospheric pressure to drive the diffused sterilant vapor further into the article to achieve sterilization. The '508, '672 and '607 Childers inventions are similar in that all three require repeated pulsations of sterilant vapor flow and maintenance of the sterilization chamber pressure at a predetermined subatmospheric pressure.

One disadvantage of the cleaning/sterilizing or cleaning/disinfecting systems of the prior art as discussed above is that, after the device is sterilized or disinfected and before it is dried, the device has to be rinsed with sterile water to remove disinfectant or sterilant residues. A bacteria filter is usually used to filter the water to remove particulates and bacteria. Typically, a two-stage filtering system is utilized; for example, a first stage has a 2–5 micron filter and a second stage has a 0.1–0.2 micron filter. However, viruses can be smaller than 0.1 micron. This means that a virus can penetrate the filtering system, recontaminating the sterilized device in the final rinsing process. Another problem associated with the use of a bacteria filter is that bacteria can form biofilms in the filter, which are difficult to sterilize and thus become a new potential source of contamination.

Thus, there remains a need for a simple and effective process and apparatus for efficiently cleaning, sterilizing, and drying medical devices, especially those with long narrow lumens.

SUMMARY OF THE INVENTION

One aspect of the present invention provides a method for cleaning or sterilizing a device, such as an endoscope, having a lumen with at least two open ends and an inner surface and outer surface. The method involves the use of a container possessing two or more openings, and a flexible, gas-impermeable pouch that surrounds the container. The device is placed into the container. A negative pressure differential is applied to the container and pouch, thereby causing the pouch to collapse around the container. "Negative pressure differential" is defined herein as the condition in which the pressure inside the container is lower than the pressure outside the container.

Upon collapsing, the pouch forms at least one interface separating the container into two or more compartments. This interface is formed by the adherence, or sealing, of the pouch onto itself and around part of a surface of the device, through openings in the container. After the interface is formed, one open end of the device is located in one of the compartments, and another open end is in another compartment. Next a flow of a cleaning solution, rinse solution, or chemical germicide is generated through the lumen of the device, to clean or sterilize the inner surface of the device.

In another aspect of the present invention, the method additionally involves lessening, removing, or not applying the negative pressure differential, causing the pouch not to seal or at least to partially unseal around the device. Then a flow of cleaning solution, rinse solution, or chemical germicide is generated around the outer surface of the device to clean or sterilize the outer surface of the device. One or more of these acts may be repeated.

In another aspect of the method, sterilizing is conducted under reduced pressure. One method of sterilization involves retaining a predetermined amount of the chemical germicide in the container and vaporizing the retained chemical germicide to sterilize the device under negative pressure differential after the pouch is collapsed. In a further aspect of the method, sterilizing is conducted by reducing pressure in the container to a first predetermined pressure, followed by further reducing the first pressure to a predetermined second pressure. Sterilizing can also be conducted at a controlled pump-down rate. In one embodiment of the method, the sterility of the device is maintained in the container after the device is sterilized.

A further aspect of the invention comprises drying the device after sterilization. One embodiment of the method further comprises removably attaching the container to a vacuum system for applying reduced pressure to the container and detaching the container after the device is sterilized. In one embodiment, the container further comprises a tray. In a further embodiment, the container has one or more additional openings to facilitate the flow of air during application of negative pressure differential, or to permit influx or efflux of fluid for purposes of cleaning or sterilizing the device.

In one aspect of the invention, the container has one or more shower heads or jet heads located on its inner aspect, to permit pressurized influx of fluid for purposes of cleaning or sterilizing the device. The flow of fluid through the lumen may be generated by creating a pressure differential between the compartments. In one aspect of the method, the flow of fluid through the lumen is from a smaller-caliber end of the device to a larger-caliber end of the device.

Apparatuses for performing the methods described above are provided for in multiple aspects of the present invention. In some embodiments, an apparatus is provided for cleaning or sterilizing a lumen device having at least two open ends. One such apparatus comprises a) a container having one or more openings for flowing fluid into and out of the container, or for evacuating air from the container during application of negative pressure differential; b) a flexible, gas-impermeable pouch that surrounds the container, having one or more openings for flowing fluid into and out of the container, or for evacuating air from the container during application of negative pressure; and c) at least one interface separating the container into two or more compartments. This interface is formed under a negative pressure differential by the adherence, or sealing, of the pouch onto itself and around part of a surface of the device, through openings in the container, with one open end of the device located in one of the compartments and another open end in another of the compartments.

In one aspect of the invention, the apparatus further comprises a cleaning mechanism adapted to clean the device in the container. In multiple embodiments, this cleaning mechanism is selected from the group consisting of a stirrer, a liquid jet, an air jet, ultrasonics, and a bubble generator. In one aspect of the invention, the container further comprises a tray, with or without a lid. The container may have one or more shower heads or jet heads on its inner aspect, to permit pressurized influx of fluid for purposes of cleaning or sterilizing the device.

In one embodiment, the container has one or more additional openings to facilitate the flow of air during application of the negative pressure differential or to permit influx or efflux of fluid for purposes of cleaning or sterilizing the device.

In one aspect of the present invention, the apparatus further comprises a vacuum system, and the container comprises a gas-permeable and microorganism-impermeable barrier and is detachably coupled to the vacuum system. This gas-permeable and microorganism-impermeable barrier can be equipped with a valve for opening and closing gas communication between the container and the vacuum system or between the container and atmosphere through the barrier. In one embodiment, the pouch is removable from the container.

DETAILED DESCRIPTION OF THE PREFERRED EMBODIMENT

Figure 1A:
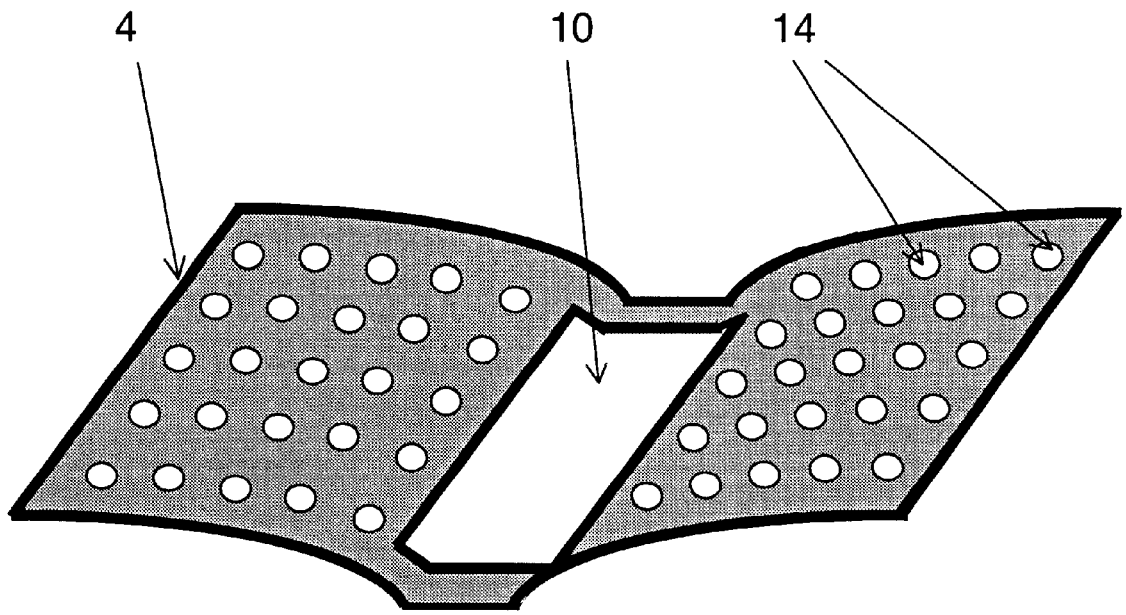
FIG. 1a is an oblique side view of a lid for a container.

Although the description below is primarily directed to the cleaning and sterilizing of endoscopes, other devices with inner channels, or lumens, can be cleaned and/or sterilized with the present invention, as will be readily apparent to one of skill in the art in view of the disclosure herein.

Method to Deliver a Predetermined Amount of Liquid Sterilant

This method can be incorporated into the cleaning/ sterilizing or cleaning/disinfecting process of the present invention. In order to maximize the efficiency of a vapor sterilization process, it is important and desirable to drain excess sterilant solution and only keep a desired amount of the sterilant solution to vaporize after treating a device to be sterilized with the sterilant solution.

According to the present invention, a cleaning or sterilization container may have a surface with wells thereon which define a known volume. The well is positioned so that when a liquid sterilant is introduced onto the surface, a known volume of the liquid sterilant fills the well. When the liquid sterilant is drained from the surface, the known volume of liquid sterilant remains in the well so that a subsequent vapor sterilization process can be performed on the device with the known volume of liquid sterilant positioned within the surface. The well formed in the surface can be curved, flat or angled. Thus, the well can be an inwardly extending hemispherical projection. The well can also be formed in the surface as an inwardly extending rectangular projection having rounded ends. The well formed in the surface can also be a rectangular box having sidewalls, defining an opening. Where perforations are provided, they can be disposed adjacent the well, and can be roughly spherical in shape. The upwardly extending projection can include a perforation thereon, which can be on top of the projection or on a side of the projection. The surface can be a sloped surface, a convex or concave surface or a V-shaped surface. The surface can be made of a variety of materials including stainless steels, aluminum, aluminum alloys, liquid crystal polymers, polyesters, polyolefins polymers or fluorinated polyolefins. If the surface is comprised of a composite material, the composite material can include a filler of high thermal conductivity. Examples of composite materials include a metal-filled polymer, a ceramic-filled polymer and a glass-filled polymer. Those materials are also suitable for the sidewalls and ends of the sterilization container.

A tray with wells with configurations similar to that described above can be provided with a container. The tray can be secured to the container or removably placed in the container.

Method Based on Diffusion-restricted Environments

A method of vapor sterilization or disinfection under diffusion-restricted environments can also be used in cooperation with the cleaning/sterilizing or cleaning/disinfecting process of the present invention. In this method, the devices (lumen or non-lumen) to be sterilized are pretreated with a sterilant solution, and then exposed to pressures less than the vapor pressure of sterilant. Both the exterior and interior surface areas of a lumen or non-lumen device can be effectively sterilized by taking advantage of the diffusion-restricted environments within lumens or within a container or enclosure.

As used herein, a "diffusion-restricted" area refers to any one or more of the following properties: (1) the ability of the area of an article placed within the sterilization system of the present invention to retain 0.17 mg/L or more hydrogen peroxide after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the starting 1 mg/L hydrogen peroxide solution initially placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

This method includes the steps of contacting the exterior and interior of a device with a sterilant solution, and then exposing the device to a negative pressure or vacuum for a period of time sufficient to effect complete sterilization. For example, when 1 mg/L of hydrogen peroxide is used as sterilant, if the exposing step is conducted for 1 hour at 40° C. and 10 torr, the diffusion restricted area preferably retains 0.17 mg/L or more hydrogen peroxide, or retains 17% or more of the hydrogen peroxide placed therein after the exposing step. In certain preferred embodiments, the diffusion-restricted area has the same or more diffusion restriction than provided by a lumen 27 cm in length and an internal diameter of 3 mm, or has the same or more diffusion restriction than provided by a lumen having a ratio of length to internal diameter greater than 50. The contacting step can be performed by either a direct or an indirect contact procedure. Direct contacting includes methods such as injection, static soak, flow-through, condensation of a vapor, or aerosol spray, or mist spray. Any other methods involving physically contacting the devices to be sterilized with a sterilant would be considered direct contacting. Indirect contacting includes those methods in which sterilant is introduced into the chamber or container, but not directly on or on the devices to be sterilized. The exposing step is preferably performed for 60 minutes or less, and is preferably performed at a pressure less than the vapor pressure of the sterilant. Thus, the preferred pressure range under conditions of the present invention is between 0 and 100 torr. The exposing step can include the step of heating the device, such as by heating the container in which the exposing step occurs. The container can be heated to about 40° C. to about 55° C. Alternatively, the sterilant solution can be heated, such as to a temperature of about 40° C. to about 55° C. Optionally, the step of exposing the device to a plasma can be conducted during the step of exposing the device to negative pressure or vacuum. In one embodiment employing exposure to plasma, the method is performed within a first chamber and the plasma is generated in a second separate chamber. This embodiment further comprises the step of flowing the plasma into the first chamber. Advantageously, the contacting and/or exposing steps of the method can be repeated one or more times.

Method Based on Controlled Pump-down Rate

The cleaning/sterilizing process of the present invention can also be carried out in cooperation with a controlled pump-down method without relying on a diffusion-restricted environment.

Effective sterilization results similar to those created in diffusion-restricted environments can be created through controlling the evacuation rate of a chamber or container in which devices to be sterilized are placed. Thus, in one embodiment of the present invention, this controlled pump-down rate method comprises the steps of contacting the device with a liquid sterilant at a first pressure; draining excess liquid sterilant to retain a predetermined amount of the sterilant, and decreasing the pressure of the chamber to a second pressure below the vapor pressure of the liquid sterilant in which at least a portion of the decrease in pressure below the vapor pressure of the liquid sterilant occurs at a pump-down rate of less than 0.8 liters per second, calculated based on the time required to evacuate the chamber from atmospheric pressure to 20 torr when the chamber is empty and dry, i.e. when the chamber has neither devices to be sterilized nor a visible quantity of liquid within it. According to one aspect of this preferred embodiment, at least the decrease in pressure below about two times the vapor pressure of the liquid sterilant occurs at a pump-down rate of less than 0.8 liters per second. According to another embodiment, the decrease in pressure below about four times the vapor pressure of the liquid sterilant occurs at a pump-down rate of less than 0.8 liters per second. Preferably, the pump-down rate is 0.6 liters per second or less; more preferably, 0.4 liters per second or less; and most preferably, 0.2 liters per second or less. Advantageously, the first pressure is atmospheric pressure. Preferably, the liquid sterilant is hydrogen peroxide. The hydrogen peroxide usually is a solution as used in the art, preferably it is a 3–60% solution. The device can be a lumen or non-lumen medical instrument.

The present invention can also incorporate a method for sterilizing a device comprising the steps of (a) contacting the device with liquid sterilant at a first pressure; (b) retaining a predetermined amount of the liquid sterilant in the container; (c) pumping down the container or chamber to a second pressure which is lower than the first pressure at a first rate; and (d) pumping down the container or chamber to a third pressure which is lower than the second pressure, wherein at least a portion of the pumping down to the third pressure is at a second rate which is slower than the first rate. The pump-down rate either above and/or below the second pressure can be constant or variable. In certain embodiments, the pump-down rate either above and/or below the second pressure is reduced in stepwise fashion. Preferably, the second pressure is greater than or equal to about the vapor pressure of the liquid sterilant; more preferably, the second pressure is greater than or equal to about two times the vapor pressure of the liquid sterilant; most preferably, the second pressure is greater than or equal to about four times the vapor pressure of the liquid sterilant. Advantageously, the pump-down rate in step (d) is 0.8 liters/sec or less; more advantageously 0.6 liters/sec or less; even more advantageously 0.4 liters/sec or less; and most advantageously 0.2 liters/sec or less, calculated based on the time required to evacuate the chamber from atmospheric pressure to 20 torr under empty and dry conditions. Preferably, the liquid sterilant is hydrogen peroxide. In another embodiment, the device is a medical instrument having a lumen. Preferably, the pumping down of step (c) reduces the pressure to less than about three times, more preferably to less than about two times, the vapor pressure of the liquid sterilant.

Another suitable method includes contacting the device with liquid sterilant, retaining a predetermined amount of the liquid sterilant in the container, and reducing the pressure of the chamber while regulating the pump-down rate so as to control the evaporation rate of sterilant in the chamber. In any of the methods described above, the contacting step may comprise application of liquid or condensed vapor. These methods described above may additionally comprise further evacuating the chamber to remove residual sterilant. Further, these methods described above may additionally comprise exposing the device to plasma to remove residual sterilant or enhance sterilization efficacy. The contacting step in these methods can be either by direct or indirect contacting. As stated herein, indirect contacting involves introducing sterilant into the chamber without directly contacting the device to be sterilized.

A. Two-Step Pump-Down Method

A two-step pump-down sterilization method can also be used in cooperation with the cleaning/sterilizing process of the present invention. This method comprises the steps of contacting a device with liquid sterilant; draining excess liquid sterilant to retain a predetermined amount of the sterilant; bringing the pressure of the chamber to a first pressure range at which the liquid sterilant is vaporized from non-diffusion restricted area of the device to sterilize the non-diffusion restricted area; bringing the pressure of the chamber to a second pressure range at which the liquid sterilant is vaporized from diffusion restricted area of the device to sterilize the diffusion restricted area, wherein the minimum pressure in the second pressure range is lower than the maximum pressure in the first pressure range.

Preferably, the first pressure range is from 20 to 760 torr; more preferably, the first pressure range is 20 to 80 torr; most preferably, the first pressure range is 40–50 torr. Advantageously, the second pressure range is 1–30 torr; more advantageously, the second pressure range is 5–10 torr. In one preferred embodiment, the device includes a diffusion-restricted environment. Preferably, the device is a medical instrument with a lumen. Advantageously, the sterilant is hydrogen peroxide. According to another aspect of this preferred embodiment, the chamber is at a set temperature and wherein the first pressure is preferably lower than the vapor pressure of the sterilant at the set temperature. Preferably, the pressure of the chamber is maintained constant at the first pressure for a time period sufficient to sterilize the non-diffusion-restricted area. Advantageously, the pressure of the chamber is maintained constant at the second pressure for a time period sufficient to sterilize the diffusion-restricted area. The pressure of the chamber may be permitted to increase after reaching the first or second pressure range as a result of vaporization of the sterilant within the chamber. Alternatively, the pressure of the chamber is permitted to decrease after reaching the first or second pressure through pumping of the chamber at a rate slower than used to decrease the pressure between the first and second pressure ranges. Preferably, the contacting step is with liquid, condensed vapor, or mist. The method can also include the steps of bringing the pressure to a third pressure lower than the second pressure to remove residual sterilant and/or exposing the device to plasma to remove residual sterilant or enhance sterilization efficacy.

Method Involving Direct Flow Through a Lumen of the Device to be Sterilized

A method of directly flowing fluid through a lumen of a medical device to be treated can be incorporated with the cleaning/sterilizing or cleaning/disinfecting process of the present invention. An apparatus can be used to efficiently clean and sterilize devices with long narrow lumens by flowing a fluid such as a cleaning solution or a sterilant, either in liquid phase or in vapor phase, or a plasma gas directly through the lumens of lumen devices to be sterilized.

The flow of a germicide (solution or vapor) or any cleaning solution through a lumen of a medical device is driven by a pressure drop between two open ends of the lumen. The pressure drop can be generated by applying either a vacuum or a high pressure at one end. By generating a forced flow through a pressure differential other than relying on diffusion, the sterilization rate is significantly increased and less time is needed for a sterilization cycle.

The two ends of the lumen need to be exposed to a pressure differential. This is achieved in the present invention by placing a sealable interface between two compartments to separate them from each other. Preferably, an opening is provided in the interface and the lumen device to be sterilized traverses the opening so that the lumen serves as a flow path between the two chambers or between the container and the enclosure.

In order to promote sterilization efficiency, all the sterilization apparatuses of the present invention can be further equipped with a heater and/or a plasma.

Several preferred embodiments of the present invention will be described with reference to the accompanying drawings.

Figure 1B:
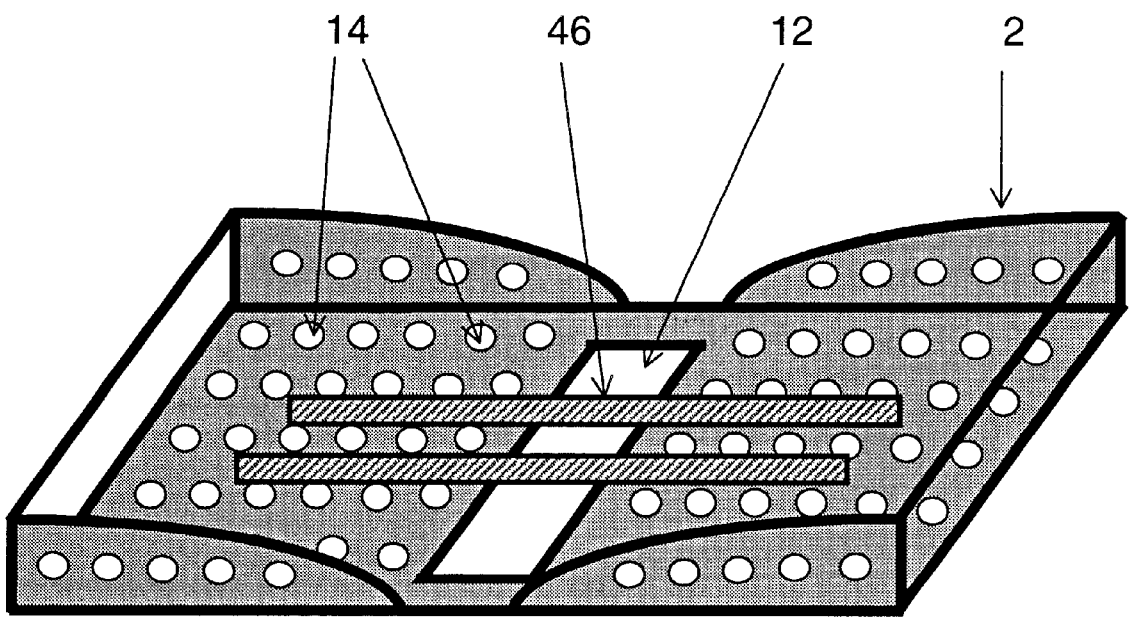
FIG. 1b is an oblique side view of a container in a tray configuration.

FIGS. 1*a* and 1*b* disclose two parts of one preferred embodiment for the container: a container 2 in a tray configuration, and a lid 4 that fits onto the container 2. Such a lid is not essential. In other embodiments, a tray will be used without a lid, and the method will work equally well. The lid 4 has a central opening 10, and the container 2 similarly has a central opening 12. In addition, both the container 2 and the lid 4 have multiple openings 14 on their surfaces, to facilitate the flow of air from the pouch (pouch 6, as shown in FIG. 1*c*, below).

One or more lumen devices 46, such as endoscopes, are placed into the container 2, and then the lid 4 is affixed to the container 2.

Figure 1C:
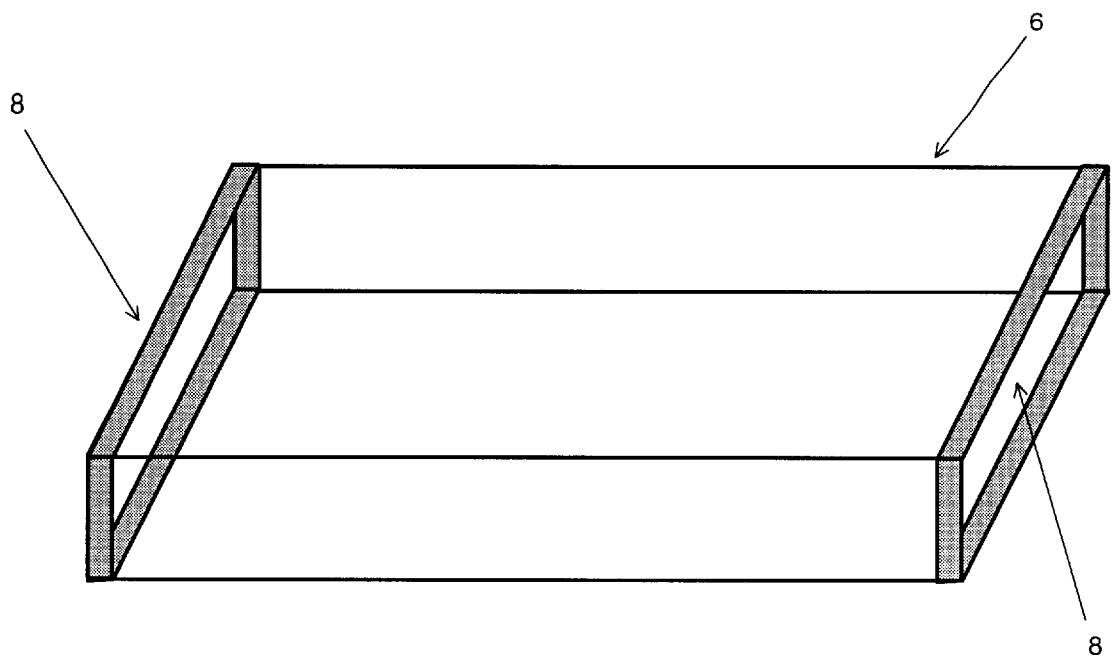
FIG. 1c is an oblique side view of the collapsible pouch.

FIG. 1*c* shows the collapsible pouch 6. In one embodiment, this pouch has openings 8 at both ends.

Figure 1D:
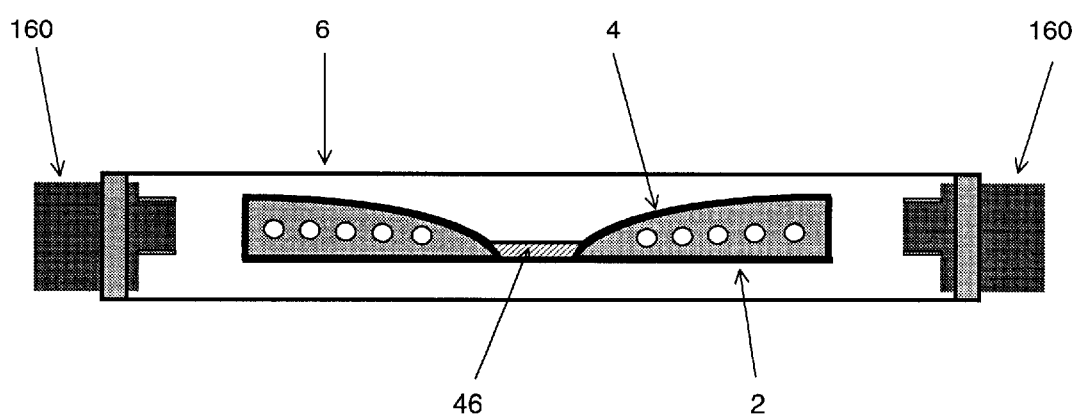
FIG. 1d is a side view of the container inside the pouch, with fluid ports attached to each end of the pouch.

Referring to FIG. 1*d*, the container 2, with lid 4 in place, is placed into the pouch 6. The open ends 8 of the pouch 6 are then attached to fluid ports 160.

Figure 1E:
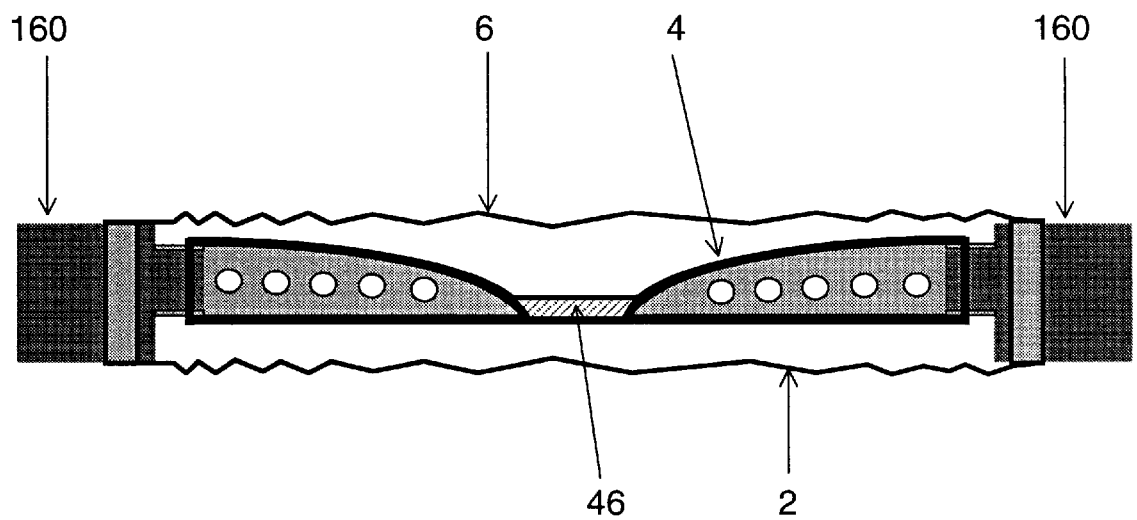
FIG. 1e is a side view of the container inside the pouch, with fluid ports attached to each end of the pouch and container.

As shown in FIG. 1*e*, the container 2 is then attached to the fluid ports 160, and a negative pressure differential is applied. "Negative pressure differential" is defined as the condition in which the pressure inside the container is lower than the pressure outside the container. This negative pressure differential may be generated by increasing pressure outside the pouch, decreasing pressure inside the pouch, or a combination of both of these maneuvers. A decrease in pressure within the pouch 6 can be produced by a vacuum pump attached to at least one of the fluid ports 160. Alternatively, the pouch 6 and container 2 can be placed into a larger container (not shown), and then air can be pumped into the larger container (not shown) under positive pressure. As a result of the positive pressure exerted on the pouch 6 and container 2 within the larger container (not shown), the pouch 6 collapses around the device 46.

Figure 1F:
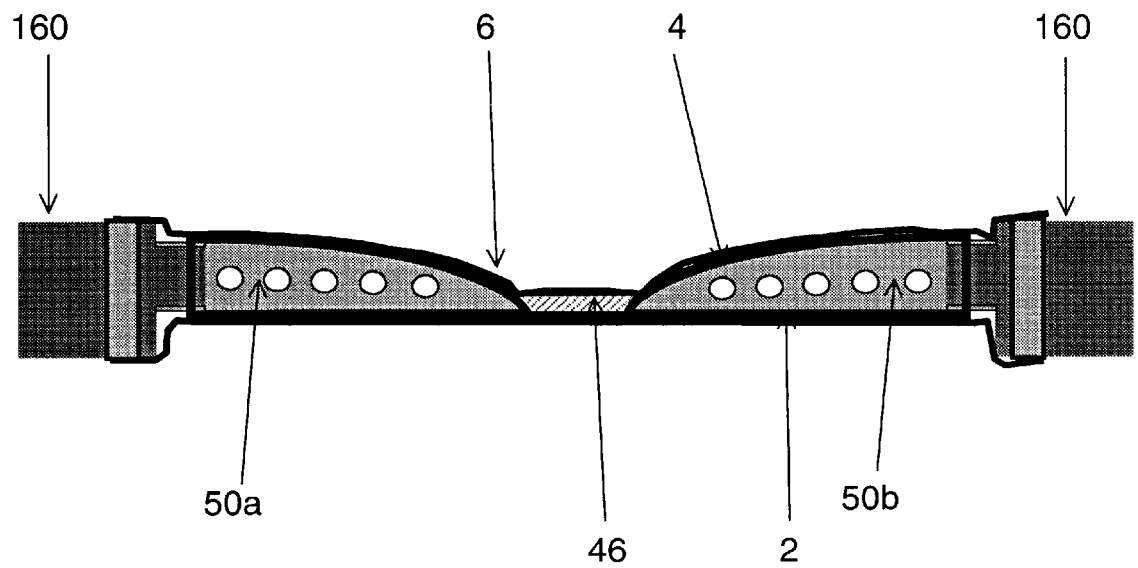
FIG. 1f is a side view of the container inside the pouch, with fluid ports attached to each end of the pouch and container, with negative pressure differential applied.

As air flows out of the container 2 and the pouch 6, the pouch 6 begins to collapse, and the pouch's inner surfaces move toward the container 2 and the lid 4. The efflux of air from the container is facilitated by the openings 14 in the container 2 and the lid 4. Referring to FIG. 1*f*, after a sufficient negative pressure differential is achieved, the pouch 6 collapses around the container 2, causing the pouch's inner surfaces to adhere to themselves through the opening 12 in the container 2 and the opening 10 in the lid 4. Furthermore, the pouch's inner surfaces adhere to at least one surface of the device 46. This area of adherence of the pouch's inner surface creates an interface that divides the container 2 into at least two compartments, 50*a* and 50*b*. At this time, one open end of the device 46 located in one (50*a*) of the compartments, and another open end is in another (50*b*) of the compartments.

A sanitizing solution, herein defined as a cleaning solution, rinse solution, and/or chemical germicide, is introduced into the container 2 through a fluid port 160. Then a flow of this fluid is generated from inside the container 2 through the inner channel, or lumen, of the device 46, from one compartment 50*a* to another compartment 50*b*, or vice versa, to clean or sterilize the inner channel of the endoscope.

In a further aspect of the present invention, a flow of cleaning solution, rinse solution, or chemical germicide is generated from inside one (50*b*) of the compartments to another (50*a*) of the compartments, or vice versa, around the outer surface of the endoscope 46, to clean or sterilize the outer surface of the endoscope 46. In another aspect of the present invention, one or more of the preceding acts are repeated.

In another aspect of the present invention, the method additionally involves lessening, removing, or not applying the negative pressure differential to the container 2 and the pouch 6, causing the pouch 6 not to seal, or at least partially to unseal, around the device 46. Then a flow of cleaning solution, rinse solution, or chemical germicide is generated from inside one (50*b*) of the compartments to another (50*a*) of the compartments, or vice versa, around the outer surface of the device 46, to clean or sterilize the outer surface of the device 46. One or more of these acts may be repeated.

In another aspect of the present invention, sterilizing is conducted under reduced pressure. One method of sterilization comprises retaining a predetermined amount of the chemical germicide in the container 2 and vaporizing the retained chemical germicide to sterilize the device 46 under reduced pressure. The pouch 6 and container 2 are placed together into a vacuum chamber (not shown), and the vacuum chamber and the container 2 are evacuated at the same time, thereby avoiding collapse of the pouch 6. Because the the pouch 6 is not collapsed, the pouch 6 does not adhere to the device 46, and the entire outer surface of the device 46 is thus exposed to the vaporized germicide. This technique allows both the lumen and the entire outer surface of the device 46 to be sterilized.

In a further aspect of the method, sterilizing is conducted by reducing pressure in the container 2 to a predetermined first pressure, followed by further reducing the first pressure to a predetermined second pressure. In the method, sterilizing can be conducted at a controlled pump-down rate. In one embodiment of the method, the sterility of the device 46 is maintained in the container 2 after the device is sterilized.

A further aspect of the invention comprises drying the device 46 after sterilization. One embodiment of the method further comprises removably attaching the container 2 to a vacuum system for applying reduced pressure to the container, and detaching the container after the device 46 is sterilized.

In one aspect of the invention, the container 2 has one or more shower heads or jet heads located on its inner aspect, to permit pressurized influx of fluid for purposes of cleaning or sterilizing the device. In one aspect of the method, the flow of fluid through the lumen is from a smaller-caliber end of the device 46 to a larger-caliber end of the device 46.

Apparatuses for performing the methods described above are provided for in multiple aspects of the present invention. In some embodiments, an apparatus is provided for cleaning or sterilizing a lumen device 46 having at least two open ends. One such apparatus comprises a) a container 2 having one or more openings for flowing fluid into and out of the container, or for evacuating air from the container 2 during application of negative pressure differential; b) a flexible, gas-impermeable pouch 6 that surrounds the container 2, having one or more openings 8 for flowing fluid into and out of the container, or for evacuating air from the container 2 during application of reduced pressure; and c) at least one interface separating the container 2 into two or more compartments (50a and 50b).

In one aspect of the invention, the apparatus further comprises a cleaning mechanism adapted to clean the device 46 in the container 2. In multiple embodiments, this cleaning mechanism is selected from the group consisting of a stirrer, a liquid jet, an air jet, ultrasonics, and a bubble generator.

In one embodiment, the container 2 has one or more additional openings 14 to facilitate the flow of air during application of the negative pressure differential or to permit influx or efflux of fluid for purposes of cleaning or sterilizing the device 46.

In one aspect of the present invention, the apparatus further comprises a vacuum system, and the container comprises a gas-permeable and microorganism-impermeable barrier and is detachably coupled to the vacuum system. This gas-permeable and microorganism-impermeable barrier can be equipped with a valve for opening and closing gas communication between the container 2 and the vacuum system or between the container 2 and atmosphere through the barrier. In one embodiment, the pouch 6 is removable from the container 2.

In a further aspect of the present invention, sterilization of the lumen device 46 is conducted under a reduced pressure. After cleaning the lumen device 46, a predetermined amount of chemical germicide may be left in the container 2. This process of leaving some chemical germicide in the container 2 is sometimes referred to as "pretreatment" by those skilled in the art, and the definition of "sterilization," as the term is used herein, comprises this process of pretreatment. The retained chemical germicide is vaporized under reduced pressure in order to sterilize the device. In an alternative embodiment of the method, the sterilization is conducted by reducing the pressure in the container 2 to a predetermined first pressure, followed by further reducing the first pressure to a predetermined second pressure. In a further embodiment of the method, the sterilization is conducted at a controlled pump-down rate, as described above.

In a further aspect of the present method, the container 2 is placed into or attached to a vacuum system, for applying reduced pressure to the container. The container 2 is then removed or detached from the vacuum system after the device is sterilized. In one embodiment, the device 46 maintains sterility in the container 2 after the device is sterilized. The method further comprises drying the device 46 in the container 2 after sterilization.

In a further aspect of the method, the flow of fluid through the lumen of the lumen device 46 is generated by applying a pressure higher than atmospheric pressure at one end of the lumen, or by applying a vacuum to one end of the lumen device.

The present invention has been described above. Many modifications and variations of the cleaning and sterilizing processes and the apparatus used in such processes may be made without departing substantially from the spirit and scope of the present invention. Accordingly, it should be clearly understood that the form of the invention described and illustrated herein is exemplary only, and is not intended as a limitation on the scope.

What is claimed is:

1. A method for cleaning or sterilizing a device having a lumen with at least two open ends and an inner surface and outer surface, said method comprising the acts of:
   a) providing a container possessing two or more openings, and a flexible pouch that surrounds said container;
   b) placing said device into said container;
   c) applying a negative pressure differential to said container and pouch, thereby causing said pouch to collapse around said container and form at least one interface separating said container into two or more compartments, which interface is formed under negative pressure differential by the adherence, through said openings in said container, of said pouch onto itself and onto at least one part of a surface of said device, such that one open end of said device is located in one of said compartments and another open end is in another of said compartments; and
   d) generating a flow of a sanitizing solution through said lumen to clean or sterilize the inner surface of said device.

2. A method of claim 1, additionally comprising lessening, removing, or not applying said negative pressure differential, causing said pouch not to seal, or at least partially to unseal, around said device, and generating a flow of said sanitizing solution around the outer surface of said device to clean or sterilize the outer surface of said device.

3. A method of claim 2, wherein one or more acts are repeated.

4. A method of claim 2, wherein the procedure of claim 2 is performed before acts c) and d) of claim 1.

5. A method of claim 1, wherein the act of sterilizing is conducted under reduced pressure.

6. A method of claim 1, further comprising retaining a predetermined amount of a chemical germicide in said container and vaporizing said retained chemical germicide to sterilize said device under negative pressure differential after act d).

7. A method of claim 6, wherein the sterilizing is conducted by reducing pressure to a first predetermined pressure, followed by further reducing said first pressure to a predetermined second pressure.

8. A method of claim 6, wherein the sterilizing is conducted at a controlled pump-down rate.

9. A method of claim 1, wherein the sterility of said device is maintained in the container after said device is sterilized.

10. A method of claim 1, further comprising drying said device after sterilization.

11. A method of claim 1, further comprising removably attaching said container to a vacuum system for applying reduced pressure to said container and detaching said container after the device is sterilized.

12. A method of claim 1, wherein said container further comprises a tray.

13. A method of claim 1, wherein said container has one or more additional openings to facilitate the flow of air during application of said negative pressure differential or vacuum, or to permit influx or efflux of fluid for purposes of cleaning or sterilizing said device.

14. A method of claim 1, wherein said container has one or more shower heads or jet heads located on its inner aspect, to permit pressurized influx of fluid for purposes of cleaning or sterilizing said device.

15. A method of claim 1, wherein the flow of fluid through said lumen is generated by creating a pressure differential between the said compartments.

16. A method of claim 1, wherein the flow of fluid through said lumen is from a smaller-caliber end of said device to a larger-caliber end of said device.

17. The method of claim 1, wherein the pouch is gas-impermeable.

18. An apparatus for cleaning or sterilizing a lumen device having at least two open ends, comprising:

a container having one or more openings for flowing fluid into and out of said container, or for evacuating air from said container during application of negative pressure;

a flexible pouch that can surround said container, having one or more openings for flowing fluid into and out of said container, or for evacuating air from said container during application of negative pressure;

at least one interface separating said container into two or more compartments, which interface is formed under negative pressure differential by the adherence, through openings in said container, of said pouch onto itself and onto at least part of a surface of said device, with one open end of said device located in one of said compartments and another open end of said device in another of said compartments.

19. An apparatus of claim 18, further comprising a cleaning mechanism adapted to clean said device in said container.

20. An apparatus of claim 19, wherein said cleaning mechanism is selected from the group consisting of a stirrer, a liquid jet, an air jet, ultrasonics, and a bubble generator.

21. An apparatus of claim 18, wherein said container further comprises a tray.

22. An apparatus of claim 18, wherein said container has one or more shower heads or jet heads on its inner aspect, to permit pressurized influx of fluid for purposes of cleaning or sterilizing said device.

23. An apparatus of claim 18, wherein said container has one or more additional openings to facilitate the flow of air during application of said negative pressure differential, or to permit influx or efflux of fluid for purposes of cleaning or sterilizing said device.

24. An apparatus of claim 18, wherein said apparatus further comprises a vacuum system, and said container comprises a gas-permeable and microorganism-impermeable barrier and is detachably coupled to said vacuum system.

25. An apparatus of claim 24, wherein said gas-permeable and microorganism-impermeable barrier is equipped with a valve for opening and closing gas communication between the container and the vacuum system or between the container and atmosphere through said barrier.

26. An apparatus of claim 18, wherein said pouch is removable from said container.

27. The apparatus of claim 18, wherein the pouch is gas-impermeable.

* * * * *